(12) United States Patent
Nekhai et al.

(10) Patent No.: US 8,278,326 B2
(45) Date of Patent: Oct. 2, 2012

(54) INHIBITORS OF PROTEIN PHOSPHATASE-1 AND USES THEREOF

(75) Inventors: Sergei Nekhai, McLean, VA (US); Dmytro Borysovich Kovalskyy, Kiev (UA)

(73) Assignee: Howard University, Washington, DC (US)

( * ) Notice: Subject to any disclaimer, the term of this patent is extended or adjusted under 35 U.S.C. 154(b) by 374 days.

(21) Appl. No.: 12/424,243

(22) Filed: Apr. 15, 2009

(65) Prior Publication Data

US 2009/0264463 A1 Oct. 22, 2009

Related U.S. Application Data

(60) Provisional application No. 61/045,561, filed on Apr. 16, 2008.

(51) Int. Cl.
*A61K 31/473* (2006.01)
*C07D 219/08* (2006.01)
(52) U.S. Cl. ........................ 514/311; 546/104
(58) Field of Classification Search .................. None
See application file for complete search history.

(56) References Cited

U.S. PATENT DOCUMENTS

| | | | |
|---|---|---|---|
| 4,559,157 | A | 12/1985 | Smith |
| 4,608,392 | A | 8/1986 | Jacquet |
| 4,820,508 | A | 4/1989 | Wortzman |
| 4,992,478 | A | 2/1991 | Geria |
| 5,175,172 | A | 12/1992 | Dietlin et al. |
| 5,703,055 | A | 12/1997 | Felgner |
| 6,593,324 | B2 | 7/2003 | Wurster et al. |
| 6,831,086 | B1 | 12/2004 | Bernhardt |
| 7,307,083 | B2 | 12/2007 | Rosini et al. |

OTHER PUBLICATIONS

International Application No. PCT/US2009/040495, International Search Report and Written Opinion of the International Searching Authority, date of actual completion of the international search—Jun. 24, 2009, 11 pages.
E. Agbottah, et al., (2005). "Antiviral activity of CYC202 in HIV-1-invected cells", J. Biol. Chem. 280(4), 3029-42, 14 pages.
T. Ammosova, et al., (2006). "Phosphorylation of HIV-1 Tat by CKD2 in HIV-1 transcription", Retrovirology 3, 78, 21 pages.
T. Ammasova, et al. (2005a). "RNA interference directed to CDK2 inhibits HIV-1 transcription", Virology, 8 pages.
T. Ammasova, et al., (2005b). "Nuclear targeting of protein phosphatase-1 by HIV-1 Tat protein", J. Biol. Chem. 280 (43), 36364-71, 8 pages.
T. Ammasova, et al., (2003). "Nuclear protein phosphatase-1 regulates HIV-1 transcription", J. Biol. Chem 278 (34), 32189-94, 6 pages.
T. Ammasova, et al., (2005c). "Dephosphorylation of CDK9 by protein phosphatase 2A and protein phosphasase-1 in Tat-activated HIV-1 transcription", Retrovirology 2: 47, 15 pages.
D. Bharucha, et al., (2002). "A protein phosphatase from human T cells augments tat transactivation of the human immunodeficiency virus type 1 long-terminal repeat", Virology 296 (1), 6-16, 11 pages.
Z. Debebe, et al., (2007). "Iron chelators ICL670 and 311 inhibit HIV-1 transcription", Virology, 11 pages.
L. Deng, et al. (2002). "HIV-1 Tat interaction with RNA polymerase II C-terminal domain (CTD) and a dynamic association with CDK2 induce CTD phosphorylation and transcription from HIV-1 promoter", J. Biol. Chem 277(37), 33922-9, 8 pages.
M. Egloff, et al. (1997). "Structural basis for the recognition of regulatory subunits by the catalytic subunit of protein phosphatase 1", Embo J 16 (8), 1876-87, 12 pages.
S. Nekhai, et al., (2007). "A novel anticancer agent ARC antagonizes HIV-1 and HCV", Oncogene 26 (26), 3899-903, 5 pages.
S. Nekhai, et al., (2000). "Cell cycle-dependent stimulation of the HIV-1 promoter by Tat-associated CAK activator", Virology 266 (2), 246-56, 11 pages.
S. Nekhai, et al., (1997). "A human primary T-lymphocyte-derived human immunodeficiency virus type 1 Tat-associated kinase phosphorylates the C-terminal domain of RNA polymerase II and induces CAK activity", J. Virol. 71 (10), 7436-41, 6 pages.
S. Nekhai, et al., (2002). "HIV-1 Tat-associated RNA polymerase C-terminal domain kinase, CDK2, phosphorylates CDK7 and stimulates Tat-mediated transcription", Biochem. J. 364 (Pt. 3), 649-57, 9 pages.
Robert E. Lutz, et al. (1976). "Antimalarials. 11. 2-Vinylogs of substituted 2-aryl-4-quinoline amino alcohols", Journal of Medicinal Chemistry, American Chemical Society, U.S. vol, 19, No. 3, pp. 407-410, 4 pages.
European Patent Office, Supplementary European Search Report mailed Mar. 9, 2012, from related European Patent Application No. 09 732 857.9, 5 pages.

*Primary Examiner* — Kamal Saeed
(74) *Attorney, Agent, or Firm* — Fitch, Even, Tabin & Flannery

(57) ABSTRACT

Inhibitors of Protein Phosphatase-1 have been shown to slow replication of HIV-1. Inhibitors of PP 1 and their use for treatment or prevention of HIV-1 infections are disclosed.

15 Claims, No Drawings

INHIBITORS OF PROTEIN PHOSPHATASE-1 AND USES THEREOF

CROSS-REFERENCE TO RELATED APPLICATION

This application claims the benefit of U.S. Provisional Patent Application No. 61/045,561, filed Apr. 16, 2008.

STATEMENT REGARDING FEDERALLY SPONSORED RESEARCH OR DEVELOPMENT

This invention was made with government support under NIH Research Grant UHI HL03679 and RCMI-NIH 5G12RR03048 awarded by the Federal Agency "National Institutes of Health". The government has certain rights in the invention.

FIELD

The present invention relates to inhibitors of Protein Phosphatase-1, and medical uses of such inhibitors. More specifically, a class of compounds is provided that inhibit PP-1. Further, methods of using PP-1 inhibitors for treating HIV-1 infections are described.

BACKGROUND

Recent investigations have shown that Protein Phosphatase-1 (PP 1) is required for transcription of HIV-1 (Ammosova, et al., J. Biol. Chem. 280, No. 43, 36364-36371 (2005)). It appears that HIV-1 Tat binds to PP1 through the $Q^{35}VCF^{38}$ sequence of the Tat, and translocates PP1 to the nucleus of an infected cell. It was envisaged that a small-molecule inhibitor of the binding of PP1 to the HIV-1 Tat should inhibit HIV-1 transcription. This should in turn provide a way to treat subjects infected with HIV-1.

SUMMARY

Compounds are provided that inhibit HIV-1 transcription. Without being bound by any theory, it is believed that the compounds inhibit interaction between PP1 and an HIV-1 Tat, thereby inhibiting HIV-1 transcription. The compounds have been shown to inhibit HIV-1 transcription in living cells. The compounds are thus useful for treating or preventing HIV-1 infections.

In one aspect, compounds of Formula (I) are provided, where Formula (I) is:

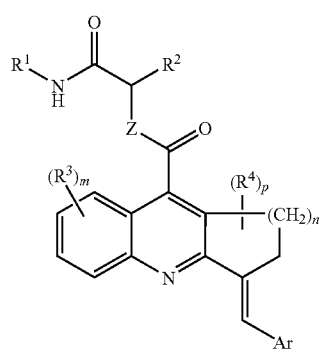

wherein n is 1 or 2;
Ar is phenyl or thienyl, and is optionally substituted;
each $R^1$ is independently $R^6$, $C(O)R^6$, $C(O)$—$OR^6$, or $C(O)N(R^6)_2$;
$R^2$ is H or optionally substituted C1-C6 alkyl, or a group of formula —C(O)NH—$R^1$;
$R^3$ is independently at each occurrence selected from halo, $NO_2$, CN, R, OR, $NR_2$;
$S(O)_qR$, COOR, and $CONR_2$, where each R is independently H, C1-C4 alkyl, or C1-C4 haloalkyl;
m is 0-4;
$R^4$ is $R^6$, halo, =O, $COOR^6$, CO $N(R^6)_2$, $S(O)_qR^6$, $N(R^6)_2$, or $OR^6$;
p is 0-2;
each q is independently 0-2;
Z is O or $NR^5$;
$R^5$ is $R^6$ or $C(O)R^6$; and
$R^6$ is independently at each occurrence selected from H, C1-C6 alkyl, C5-C6 aryl, and (C5-C6-aryl)-C1-C6 alkyl, where each alkyl and aryl is optionally substituted;
provided that n is 2 when Z is O and Ar represents para-halophenyl;
or a pharmaceutically acceptable salt thereof.

Pharmaceutical compositions are provided that include at least one compound of formula (I) and other compounds described herein are admixed with a pharmaceutically acceptable excipient. The use of the compounds of formula (I) and other compounds described herein for manufacture of a medicament, especially a medicament for the treatment of HIV infected subjects are provided.

In another aspect, methods are provided to treat or prevent an HIV-1 infection by administering to a subject in need thereof an effective amount of a compound of formula (I) and other compounds described herein. The methods include various routes of administration for the compounds of formula (I) and other compounds described herein as well as use of a compound of formula (I) in combination with other therapeutic agents effective for the treatment or prevention of HIV-1 infections.

DETAILED DESCRIPTION

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10 C or as C1-C10 or 1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10 C(alkyl) or 2-10 C (alkenyl or alkynyl). Preferably they contain 1-8 C (alkyl) or 2-8 C (alkenyl or alkynyl). Sometimes they contain 1-4 C (alkyl) or 2-4 C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, $NR'COOR'$, NR'COR', CN, COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-30, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)$NR_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. 'Aryl' can include aromatic ring systems containing only carbon as well as aromatic ring systems containing one or more heteroatoms (O, N or S) as ring members. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any mono cyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenyl ethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)— and —$C(Me)_2$— may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R7 is alkyl, this alkyl may optionally be substituted by the remaining substituents listed as embodiments for R7 where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example. In some embodiments, where no number of substituents is specified, the number is preferably 0-2.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", as used herein includes fluoro, chloro, bromo and iodo. Fluoro and chloro are often preferred.

"Haloalkyl" as used herein includes alkyl groups having one or more halogen substituents. Examples include trifluoromethyl, 2,2,2-trifluoroethyl, 2-chloroethyl, 2-fluoroethyl, and the like.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Where isomers are possible, the invention includes each individual isomer as well as mixtures of isomers. Where a chiral center is present, the invention includes each individual enantiomer at the chiral center as well as mixtures of enantiomers, including racemic mixtures.

In one aspect, the invention provides compounds that inhibit PP1. In some embodiments, the compounds are of formula (I):

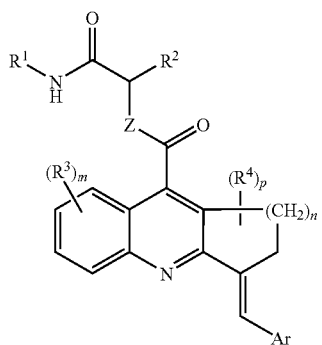

(I)

wherein n is 1 or 2;
Ar is phenyl or thienyl, and is optionally substituted;
each $R^1$ is independently $R^6$, $C(O)R^6$, $C(O)$—$OR^6$, or $C(O)N(R^6)_2$;
$R^2$ is H or optionally substituted C1-C6 alkyl, or a group of formula —$C(O)NH$—$R^1$;
$R^3$ is independently at each occurrence selected from halo, $NO_2$, CN, R, OR, $NR_2$; $S(O)_qR$, COOR, and $CONR_2$, where each R is independently H, C1-C4 alkyl, or C1-C4 haloalkyl;
m is 0-4;
$R^4$ is $R^6$, halo, =O, $COOR^6$, $CON(R^6)_2$, $S(O)_qR^6$, $N(R^6)_2$, or $OR^6$;
p is 0-2;
each q is independently 0-2;
Z is O or $NR^5$;
$R^5$ is $R^6$ or $C(O)R^6$; and
$R^6$ is independently at each occurrence selected from H, C1-C6 alkyl, C5-C6 aryl, and (C5-C6-aryl)-C1-C6 alkyl, where each alkyl and aryl is optionally substituted;
provided that n is 2 when Z is O and Ar represents para-halophenyl; or a pharmaceutically acceptable salt thereof.

In some embodiments, Z is $NR^5$. In such embodiments, $R^5$ is sometimes H and it is sometimes —C(O)R', where R' is a C1-C4 alkyl or C1-C4 haloalkyl. In other embodiments, Z is O or NH; preferably Z is O.

In some embodiments, Ar is phenyl, which is optionally substituted. Preferably, wherein is 1, Ar is not 4-halophenyl.

In other embodiments, Ar is thienyl, which can be substituted. Thienyl can be attached at either position 2 or position 3 of the thiophene ring. In some embodiments, Ar is 2-thienyl, and is optionally substituted. In other embodiments, Ar is optionally substituted 3-thienyl.

In some embodiments, n is 1. In some embodiments, n is 2.

In some embodiments, $R^2$ is H or C1-C4 alkyl or C1-C4 haloalkyl. Preferably, $R^2$ is H, methyl or ethyl.

In some embodiments, m is O. In other embodiments, m is 1-2.

In some embodiments, when m is not 0, at least one $R^3$ is halo, Cl-C4 alkyl, or C1-C4 haloalkyl.

In some embodiments, p is O. In other embodiments, p is 1-2.

Where p is not 0, in some embodiments at least one $R^4$ is =O, C1-C4 alkyl, or C1-C4 haloalkyl.

In some embodiments, $R^1$ is an optionally substituted C1-C6 alkyl. In other embodiments, $R^1$ is $C(O)R^6$. In other embodiments, $R^1$ is $C(O)NHR^6$.

The compounds of formula (I) readily form acid addition salts. In some embodiments, the compound of formula (I) is an acid addition salt. In many embodiments, the acid addition salt is a pharmaceutically acceptable salt.

Some specific compounds that have been shown to inhibit HIV-1 transcription with effective concentration (IC-50) of about 10 micromolar or less include:

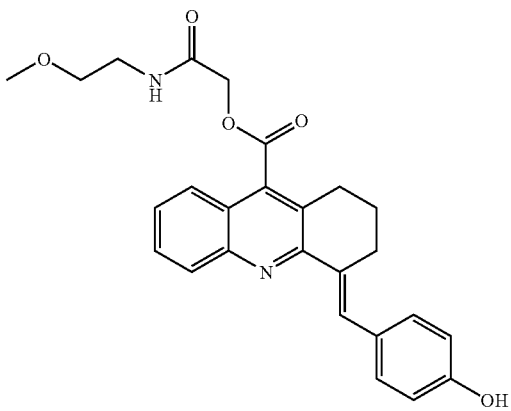

A

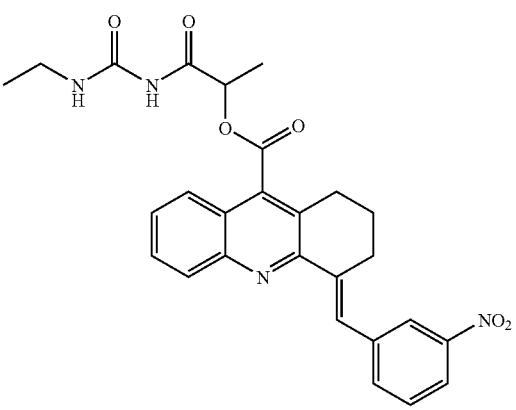

B

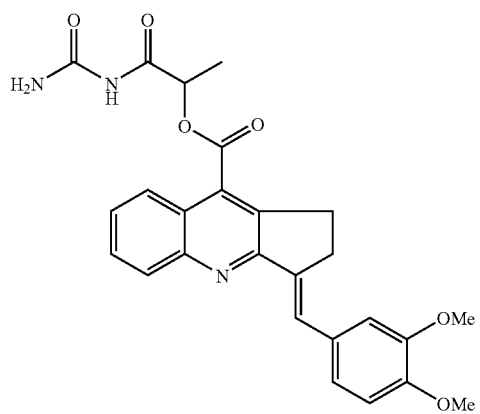

C

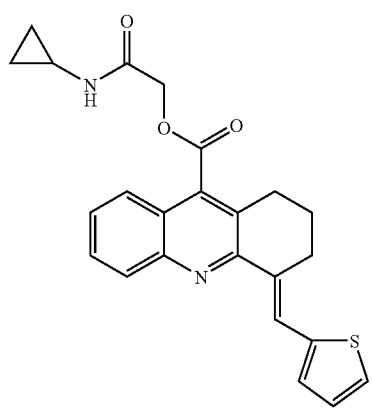

D

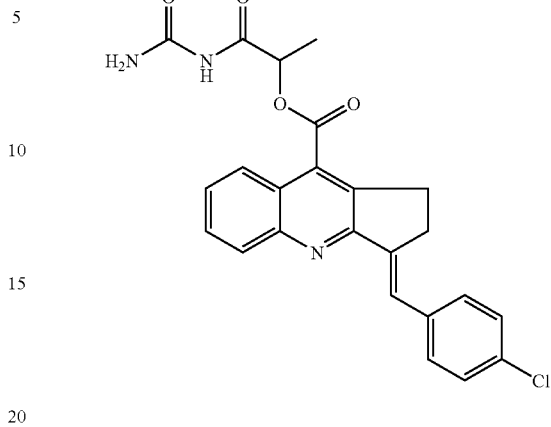

E

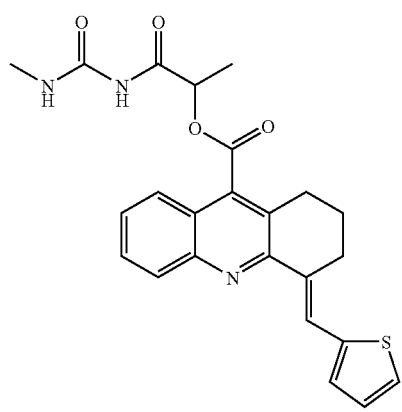

Table 1 provides some data showing efficacy of selected compounds for inhibition of Tat-induced transcription of HIV-1 in two cell lines. It also provides a qualitative assessment of the toxicity of the compounds in those cell lines, and shows that one compound (Compound A) inhibited HIV-1 replication by 50% at 10 μM.

TABLE 1

Bioactivity Data for Selected Compounds.

| Cmpd. | Transcription inh. in CEM cells (IC-50) | Transcription inh. in 293T cells (IC-50) | 50% Inh. of HIV replication | Toxicity in CEM cells | Toxicity in 293T cells |
|---|---|---|---|---|---|
| A | 10 μM | 5 μM | 10 μM | Non | Non |
| B | 2 μM | 3 μM | N/A | Non | Non |
| C | N/A | 1 μM | N/A | Non | Non |

The following compound with a similar structure was found to be ineffective for inhibition of HIV-1 transcription, and appeared to increase the rate of transcription instead. Because of this compound's lack of activity, it is excluded from the scope of the invention; accordingly, compounds wherein Ar is 4-halo are excluded when n is 1 and Z is O.

The compounds described herein can be prepared using well-known reactions, starting from available starting materials such as 1,2,3,4-tetrahydroacridine-9-carboxylic acid as summarized in Scheme 1. This acid can readily be converted to an ester or an amide to provide compounds wherein Z is O or N, respectively, using standard conditions that are well known in the art. The wide array of available alcohols and amines enables one to synthesize many compounds with various $R^1$ and $R^2$ groups incorporated. Once an ester or amide is formed from the carboxylate, the intermediate ester or amide can be condensed with various available aldehydes to introduce the "Ar—CH=" group on the saturated ring, using a base such as potassium tert-butoxide in a polar, aprotic solvent such as DMSO, DMF, DME, or THF, or in a non-nucleophilic protic solvent such as t-butanol. It is also possible to form a hindered ester of the starting carboxylic acid, such as a t-butyl ester, and condense the acridine ester with an aldehyde as described, then hydrolyze the ester to make an intermediate carboxylic acid compound having the Ar—CH= group in place. This intermediate can then be coupled to various available or readily accessible alcohols or amines to produce the products of formula (I). Methods for such coupling reactions are well known in the art.

Scheme 1: Synthesis of compounds of Formula (I).

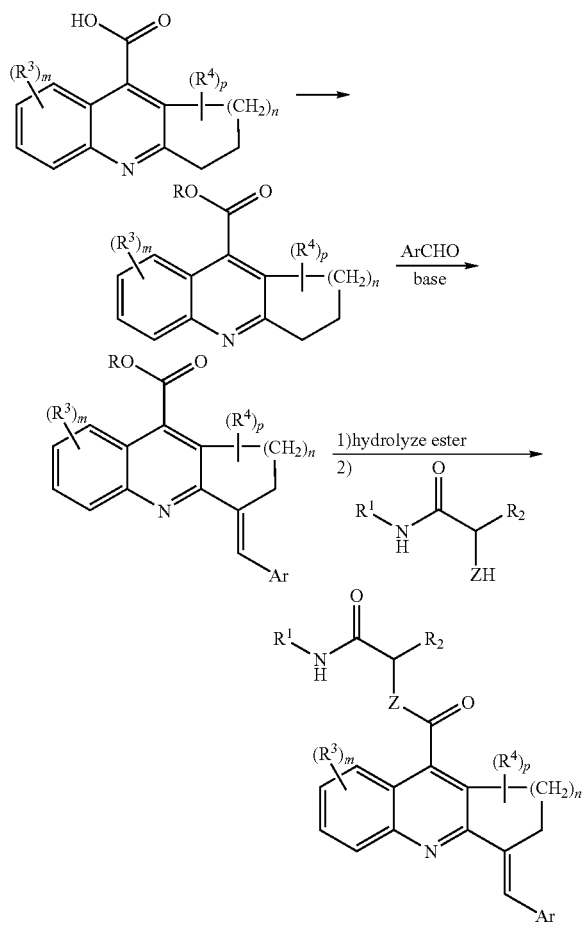

The compounds described herein are shown to be effective inhibitors of replication of HIV-1 in cell lines. Accordingly, the compounds are useful to treat or prevent HIV-1 infections in animals, including humans. Use of the compounds includes administering to a subject in need thereof an effective amount of a compound of formula I or other compounds described herein or pharmaceutical compositions thereof. Pharmaceutical compositions comprising an effective amount of at least one compound of Formula I or other compounds described herein are provided and include at least one compound of Formula I or other compounds described herein admixed with at least one pharmaceutically acceptable excipient. In some embodiments, the method includes identifying a subject in need of such treatment. The compounds described herein may be used for the manufacture of a medicament, and for the manufacture of a medicament for the treatment of HIV-1.

The compounds of Formulas I and other compounds described herein may be administered by oral, parenteral (e.g., intramuscular, intraperitoneal, intravenous, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. Methods and formulations for each of these routes of administration are within the knowledge and expertise of a person of ordinary skill in the art.

It is also contemplated that the compounds of the present invention may be used in combinations with one or more agents useful in the prevention or treatment of HIV. Examples of such agents include: (1) nucleotide reverse transcriptase inhibitor such as zidovudine, didanosine, lamivudine, zalcitabine, abacavir, stavudine, adefovir, adefovir dipivoxil, fozivudine todoxil, etc.; (2) non-nucleotide reverse transcriptase inhibitor (including an agent having anti-oxidation activity such as immunocal, oltipraz, etc.) such as nevirapine, delavirdine, efavirenz, loviride, immunocal, oltipraz, etc.; and (3) protease inhibitors such as saquinavir, ritonavir, indinavir, nelfinavir, amprenavir, palinavir, lasinavir, etc.

The scope of combinations of compounds of Formulas I and other compounds described herein with other HIV agents is not limited to (1), (2), and or (3), but includes in principle, any combination with any pharmaceutical composition useful for the treatment of HIV. Further, in such combination treatments the compounds of the present invention and other HIV agents may be administered separately or in conjunction, as a single composition or as separate compositions. In addition, the administration of one element may be prior to, concurrent to, or subsequent to the administration of other agent(s).

The compounds of Formulas I and other compounds described herein are all used to treat animals, including but not limited to, mice, rats, horses, cattle, sheep, dogs, cats, and monkey. The compounds described herein are also effective for use in humans.

The compounds of Formulas I and other compounds described herein may form hydrates or solvates, which are included in the scope of the claims. When the compounds of Formulas I and other compounds described herein exist as regioisomers, configurational isomers, conformers, or diasteroisomeric forms, all such forms and various mixtures thereof are included in the generic formulas. It is possible to isolate individual isomers using known separation and purification methods, if desired. For example, when a compound of Formulas I is a racemate, the racemate can be separated into the (S)-compound and (R)-compound by optical resolution. Individual optical isomers and mixtures thereof are included in the scope of the generic formula.

The compounds of the invention can be used in their neutral form, or as a salt. The compounds of formula I and other compounds described herein readily form acid addition salts, and in some embodiments, the acid addition salts are preferable for use in the methods and pharmaceutical compositions of the invention. Formation of such salts is within the ordinary level of skill in the art, and can be achieved by contacting a compound of formula I or other compounds described herein with a suitable acid. The salt used can be any stable salt; in some embodiments, the acid is selected to provide a pharmaceutically acceptable salt. Examples of pharmaceutically acceptable salts are organic acid addition salts formed with acids that form a physiological acceptable anion, for example, tosylate, methanesulfonate, besylate, acetate, formate, citrate, malonate, tartrate, succinate, benzoate, ascorbate, a-ketoglutarate, lactate, and a-glycerophosphate. Suitable inorganic salts may also be formed, including hydrochloride, sulfate, bisulfate, phosphate, nitrate, hydrobromide, and the like.

Compositions are provided that include a pharmaceutically acceptable carrier or diluent and an effective amount of a compound of Formula I or other compounds described herein. The pharmaceutical compositions preferably comprise at least one acceptable diluent or excipient other than water, methanol, ethanol, or DMSO. In some embodiments, the pharmaceutical composition comprises at least one excipient selected from a buffer, saline, and a mono- or di-saccharide.

A compound of Formulas I and other compounds described herein may be administered alone or as an admixture with a pharmaceutically acceptable carrier (e.g., solid formulations such as tablets, capsules, granules, powders, etc.; liquid formulations such as syrups, injections, etc.) and may be orally or non-orally administered. Examples of non-oral formulations include injections, drops, suppositories, and pessaries.

In the treatment or prevention of conditions in a human subject, an appropriate dosage level will generally be about 0.01 to 500 mg per kg patient body weight per day which can be administered in singe or multiple doses. Preferably, the dosage level will be about 0.1 to about 100, or from about 0.1 to about 10 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703,055 (Felgner, et al.) and Gregoriadis, Liposome Technology vols. I to II (2nd ed. 1993).

The pharmaceutical dosage forms suitable for injection or infusion can include sterile aqueous solutions or dispersions or sterile powders comprising the active ingredient that-are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortman (U.S. Pat. No. 4,820,508).

Compounds may be formulated with a solid carrier, which can include finely divided solids such as talc, clay, microcrystalline cellulose, silica, or alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carriers) and/or excipient(s) in liquid form or finely divided solid form, or both, and then shaping the product if required. The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

Methods for assessing the activity of compounds of the invention against HIV-1 transcription are well known in the art and were used to test compounds of the invention for activity.

The following examples describe various aspects of the invention. These examples should not be interpreted as limiting the scope of the present invention as described in the accompanying claims. Unless otherwise specified all parts and percentages are by weight and reported measurements and other data were obtained under ambient conditions.

EXAMPLE

Example 1

Screening of Compounds

Compound database preparation: X-ray coordinates of the RVSF sequence of the GM peptide bound to PP1 (courtesy of David Barford (Egloff et al., 1997)) were used for a virtual screen of Enamine's stock collection (www.enamine.net) using QXP as a docking engine and original filters for data processing. Enamine's stock was processed according to drug-like rules with two exceptions: (i) 280<MW<550 and (ii) Rotatable bonds<10. Over 300 000 compounds were analyzed in silico to generate a targeted library of 262 small molecular weight compounds (MW~500 Da).

Identification of the inhibitory compounds: The library was analyzed for the inhibition of HIV-1 transcription using reporter CEM GFP cells (courtesy of AIDS Reagents Program, NIH) that were infected with adenovirus expressing HIV-1 Tat activator protein (Ad-Tat) as previously described (Nekhai et al., 2007). Infection of CEM-GFP cells with Adeno-Tat induced HIV-1 transcription that was measured as gain of GFP fluorescence (Nekhai et al., 2007). Compounds were added at 25 μM concentration to the Ad-Tat-infected CEM-GFP cells and incubated for 24-48 hours. Cytotoxicity was evaluated by the uptake of propidium iodide (PI). The initial screening identified over 70 compounds that inhibited HIV-1 transcription at least by 75% at 25 M concentration (see Table 2 below).

TABLE 2

Analysis of 262 small molecule compounds for the inhibition of HIV-1 transcription in CEM GFP cells.

Plate 1

| | 1 | 2 | 3 | 4 | 5 | 6 | 7 | 8 | 9 | 10 | 11 | 12 |
|---|---|---|---|---|---|---|---|---|---|---|---|---|
| A | ▓ | 7.7 | 1.4 | 0.1 | ▓ | 26.9 | 64.7 | 31.5 | ▓ | 30 | 23.1 | ▓ |
| B | 46 | 24.4 | 42.3 | 41.6 | 69 | 73.9 | ▓ | 53.1 | 34.2 | 25.4 | 72.5 | 17.2 |
| C | ▓ | 54.3 | 54.5 | 58.7 | 56.4 | 52.2 | ▓ | 40.8 | 60.7 | 32 | 52.8 | 64.3 |
| D | 56.8 | ▓ | 56.5 | 55.6 | 54.4 | 70.9 | 46.1 | 48.6 | 39.2 | 14.2 | 54.7 | ▓ |
| E | 45.6 | 40.4 | 29.7 | 59.6 | 53.8 | 48.9 | 74.2 | 41.1 | 38.7 | 64.1 | 34.7 | 20.9 |
| F | 42.2 | 51.9 | 49.5 | 55.7 | 52.3 | 50.9 | 60.4 | 63.1 | 45.6 | 36.3 | ▓ | ▓ |
| G | 32.8 | 45 | ▓ | 50.3 | 45.6 | 41.4 | 45.5 | -0.2 | 45.9 | ▓ | 32.1 | 77.8 |
| H | 52.7 | ▓ | 51.4 | ▓ | 32.8 | 72.3 | ▓ | 35.7 | 56.2 | 69.3 | 51.9 | 21.4 |

Plate 2

| | 1 | 2 | 3 | 4 | 5 | 6 | 7 | 8 | 9 | 10 | 11 | 12 |
|---|---|---|---|---|---|---|---|---|---|---|---|---|
| A | 60.1 | 2.4 | -1.1 | 59.2 | 47.5 | ▓ | 12.6 | 59.1 | 28 | 26 | 5.1 | 7.1 |
| B | 31.1 | 67.5 | 33.7 | 66.5 | ▓ | 69.1 | ▓ | ▓ | ▓ | 65.2 | 59.8 | 34.2 |
| C | 63.1 | ▓ | ▓ | ▓ | ▓ | ▓ | ▓ | 69.3 | 76.5 | ▓ | 55.5 | ▓ |
| D | 65.5 | ▓ | ▓ | ▓ | ▓ | 68.1 | 68.8 | ▓ | 64.3 | 61.3 | 59.7 | ▓ |
| E | 61.1 | ▓ | ▓ | 77.1 | 69.2 | 69.2 | 76.4 | 71.5 | ▓ | 69.2 | 54.9 | 56.9 |
| F | 65.5 | 73.9 | ▓ | 69 | 76.9 | 71.2 | ▓ | 65.8 | 71.1 | ▓ | 61.3 | 42.4 |
| G | ▓ | 64.4 | ▓ | ▓ | 69.9 | ▓ | 73.6 | 72.7 | 77.9 | ▓ | 73.6 | 63.1 |
| H | 68.9 | 75.7 | 75.7 | 69.3 | ▓ | 54.7 | 68.7 | 73.5 | ▓ | 64.7 | 54 | 54.7 |

TABLE 2-continued

Analysis of 262 small molecule compounds for the inhibition of HIV-1 transcription in CEM GFP cells.

Plate 3

|   | 1 | 2 | 3 | 4 | 5 | 6 | 7 | 8 | 9 | 10 | 11 | 12 |
|---|---|---|---|---|---|---|---|---|---|----|----|----|
| A | 24.3 | 82.6 | 80 | 83 | 42.2 | 91.2 | 38.5 | 93.5 | 77.5 | | | |
| B | 23.4 | 57.2 | 55.9 | 52.7 | 62.8 | 44.7 | 70 | 74 | 92.5 | | | |
| C | 84.4 | 96.4 | 51.2 | 77.8 | 75 | 41.7 | 61.1 | 93.7 | 63.7 | | | |
| D | 59.3 | 62.4 | 52.9 | 74.6 | 48.4 | 40.3 | 87.2 | 57.3 | 54.3 | | | |
| E | 96.6 | 76.2 | 74.2 | 57.2 | 51.5 | 48.1 | | 41.6 | 51.4 | | | |
| F | 75.7 | 52.5 | 75.7 | 66 | 62.2 | 61.6 | 56 | 95.1 | 47.7 | | | |
| G | 97.7 | 79.4 | 51 | 51.8 | 58.7 | 45.7 | 45.4 | 46.8 | | | | |
| H | 47.5 | 43.6 | 42.7 | 71.9 | 79.1 | 70.6 | 89.5 | 89.8 | | | | |

Percent of inhibition is shown.
Compounds chosen for further analysis are shown in gray.

Selected compounds (69 compounds from Table 1, marked as gray shadow) were further evaluated to determine their IC50s and also cellular toxicity. Analysis of these compounds identified number of compounds that were inhibitory (Table 2).

TABLE 3

Selected compounds that shown inhibition of HIV-1 transcription.

| Plate id | well | IC50 in CEM-GFP cells | IC50 in 293T | Toxicity (PI) |
|----------|------|-----------------------|--------------|---------------|
| Plate 01 | G03 | ~7 μM | >40 μM | - |
| Plate 01 | H04 | ~10 μM | ~5 μM | - |
| Plate 01 | B07 | ~25 μM | | - |
| Plate 01 | C07 | ~10 μM | >10 μM | + |
| Plate 01 | G10 | ~20 μM | | - |
| Plate 01 | D12 | ~20 μM | | - |
| Plate 02 | D02 | ~25 μM | | - |
| Plate 02 | C03 | ~25 μM | >10 μM | + |
| Plate 02 | D03 | <10 μM, but only 50% | | + |
| Plate 02 | G03 | ~17 μM | | + |
| Plate 02 | C04 | >10 μM | | - |
| Plate 02 | C05 | >10 μM | | - |
| Plate 02 | B07 | ~6 μM | | - |
| Plate 02 | E09 | ~25 μM | >10 μM | - |
| Plate 02 | G10 | ~25 μM | | - |
| Plate 02 | D12 | ~6 μM | | - |
| Plate 03 | E01 | ~25 μM | | - |
| Plate 03 | G01 | ~25 μM | | + |
| Plate 03 | C02 | >10 μM | | - |
| Plate 03 | F03 | >10 μM | | - |
| Plate 03 | A06 | >10 μM | >10 μM | - |
| Plate 03 | A08 | >10 μM | >10 μM | - |
| Plate 03 | C08 | >10 μM | >10 μM | + |

Non-toxic compounds with IC50s less than 10 μM are shown in gray shadow.

The compounds from Table 2 were further evaluated using 293T cells transfected with Tat- and HIV-1 LTR-LacZ. FIG. 1A shows an example of inhibition of transcription and measurements of cytotoxicity by the compounds encoded as 1H4, 3C8, 1G3 and 1C7. The compounds 1H4 and 3C8 were not toxic and inhibited HIV-1 transcription (FIG. 1A). In contrast, 1C7 compound potently inhibited HIV-1 transcription but also demonstrated a high cytotoxicity (FIG. 1A). The 1G3 compounds was neither inhibitory nor toxic (FIG. 1A). Compounds 1H4, 3C8, and 1G3 were further evaluated in 293T cells transfected with Tat-expressing vector, HIV-1 LTR-LacZ reporter and CMV-EGFP reporter. Inhibitory properties of these compounds were evaluated using 293T cells transfected with Tat-expressing vector, HIV-1 LTR-LacZ reporter and CMV-EGFP reporter (Ammosova et al., 2005a). 293T cells were transfected with lipofectamine and then treated with each of the selected compounds for 18 hours. Then the cells were lysed and GFP and β-galactosidase activity was determined as we previously described (Ammosova et al., 2005a). Compound 1H4 was the most inhibitory with IC50=5 μM (FIG. 1B). The 1C7 compound did not inhibit Tat-induced HIV-1 transcription in this system (not shown). Neither of the compounds was cytotoxic as determined by LDH assay (not shown).

HIV-1 replication is inhibited by a small molecular mimetic of QVCF peptide. The 1H4 compound was evaluated to determine whether it could inhibit HIV-1 replication. MT4 cells were infected with recombinant pNL4-3 HIV-1 and treated with different concentrations of 1H4 compound and as a control 1G3 compound. The 1H4 compound inhibited HIV-1 replication at 10 μM or 25 μM concentrations (FIG. 2). The 1G3 compound did not inhibit HIV-1 replication but in contrast induced it by about 2-fold (FIG. 2). Thus, the 1H4 compound inhibits HIV-1 replication.

The 1H4 compound docks to the PP1 and inhibits Tat-PP1 interaction in vitro. A typical regulatory subunit of PP1 contains at least one RVxF motif, which directly interacts with a hydrophobic pocket on the surface of PP1. Interaction of the 1H4 with PP1 was analyzed by its docking using computer modeling. Docking shows that 1H4 occupies the hydrophobic sites of the RVTF peptide but also interacts with PP1 through additional binding sites.

To determine whether the 1H4 compound binds directly to the RVxF-binding pocket of PP1, a competition assay was conducted with Tat that was previously showed to bind to the RVxF pocket of PP1 in vitro (Ammosova et al., 2005b). Competition assays were performed with 4 nM PP1 in glycylglycine buffer. Excess of Tat inhibited PP1 (FIG. 3A, lane 3) whereas Tat QACA mutant did not inhibit PP1 (FIG. 3A, lane 4). Addition of 50 μM 1H4 to the Tat and PP1 relieved Tat-mediated inhibition of PP1 (FIG. 3A, lane 5) whereas the 50 μM 1G3 did not affect Tat-mediated inhibition of PP1 (FIG. 3A, lane 6). To analyze if 1H4 compound has an effect on the activity of CDK2 we incubated recombinant CDK2/cyclin E with histone H1 without or with the addition of increasing concentrations of 1H4. As show on the FIG. 4B, 1H4 did not have a significant effect on the activity of CDK2 suggesting that inhibition of HIV-1 transcription by 1H4 was not due to the inhibition of CDK2.

Identification of addition inhibitors. The 1H4 compound was used to create a second library of compounds that would have similar backbone as 1H4. This second library contained 143 compounds. These compounds were analyzed for the inhibition of HIV-1 transcription and toxicity in CEM T-cells and 293T cells similar as described above for the analysis of the first library. Results shown in Table 4 show that several compounds were inhibitory. Two compounds were chosen, 1E07 (T5236177) and 2F02 (T5430740) (shaded), because there were not toxic in the propidium iodide uptake assay and inhibited HIV-1 transcription both in CEM and 293T cells.

TABLE 4

Selected compounds from the 1H4-based library that shown inhibition of HIV-1 transcription.

| ID | Plate id | well | Inhibition of HIV-1 Transcription CEM IC$_{50}$ | Inhibition of HIV-1 Transcription 293T IC$_{50}$ | Toxicity in CEM cells (PI) | Toxicity in CEM (Trypan blue) | Toxicity in CEM (calcein) |
|---|---|---|---|---|---|---|---|
| T0507-8302 | Plate 01 | A02 | 3 µM | >>10 µM | not toxic | 13 µM | |
| T0515-1487 | Plate 01 | B04 | 7.5 µM | >>10 µM | not toxic | | |
| T0515-5982 | Plate 01 | D04 | 10 µM | 5 µM | not toxic | | |
| T0516-0241 | Plate 01 | H04 | 10 µM | >>10 µM | not toxic | | |
| T0516-8237 | Plate 01 | B05 | 10 µM | 4 µM | not toxic | | |
| T0519-1220 | Plate 01 | D05 | 10 µM | 0.1 µM | toxic | 2 µM | 2 µM |
| T5227431 | Plate 01 | E06 | 10 µM | 5 µM | not toxic | | |
| T5229576 | Plate 01 | G06 | 5 µM | 4 µM | not toxic | | |
| T5236177 | Plate 01 | E07 | 2 µM | 3 µM | not toxic | 9 µM | 10 µM |
| T5333787 | Plate 01 | D09 | 15 µM | 4 µM | not toxic | | |
| T5399927 | Plate 01 | C10 | 8 µM | >>10 µM | not toxic | | |
| T5400634 | Plate 01 | D10 | 8 µM | 4 µM | not toxic | | |
| T5423152 | Plate 02 | C02 | 6 µM | 4 µM | not toxic | | |
| T5430740 | Plate 02 | F02 | 6 µM | 0.2 µM | not toxic | 17 µM | |
| T5434998 | Plate 02 | B03 | 10 µM | 6 µM | not toxic | | |
| T5448953 | Plate 02 | A05 | 5 µM | 0.1 µM | toxic | 26 µM | |
| T5578540 | Plate 02 | A06 | 12 µM | 10 µM | not toxic | | |
| T5754083 | Plate 02 | A08 | 1 µM | 3 µM | toxic | 2 µM | 2 µM |

Diversified libraries of compounds based on the 1E07 structure (80 compounds) were created. These compounds were analyzed for the inhibition of HIV-1 transcription in 293T cells. The results shown in Table 5 indicated that two compounds were inhibitory: B03 (T5251792) and E06 (T5294712). However, the IC50s were similar to 1E07 and 2F02 compounds.

TABLE 5

Selected compounds from the 1E07-based diversified library that shown inhibition of HIV-1 transcription.

| ID | well | IC50 in 293T cells | Comments | Toxicity in CEM (Trypan blue) | Toxicity in CEM (calcein) |
|---|---|---|---|---|---|
| T5236177 | A01 | ~2 µM | 1E07 (second library) | | |
| T5430740 | B01 | ~2 µM | 2F2 (second library) | | |
| T5219456 | A02 | >5 µM | | | |
| T5251792 | B03 | ~1 µM | | ~100 µM | ~1 mM |
| T5402355 | G04 | >10 µM | | | |
| T5762096 | D06 | >10 µM | | | |
| T5294712 | E06 | ~2 µM | | ~100 µM | |
| T0519-1220 | A09 | >10 µM | | | |
| T5230167 | E09 | >10 µM | | | |

Compounds 1H4, 1E07, B03 and as a control 1G3 were analyzed for inhibition of HIV-1 replication and results are shown in Table 6. Both 1H4 and 1E07 inhibited HIV-1 replication with IC50 similar to those that we observed for the inhibition of HIV-1 transcription in CEM and 293T cells. Surprisingly, B03 compound was not inhibitory, which was contrary to observations.

TABLE 6

Inhibition of HIV-1 replication by 1H4 and 1E07 compounds.

| ID | Name | IIIB, IC50 | Q148R, IC50 | N155H, IC50 |
|---|---|---|---|---|
| T0513-4428 | 1G3 | 37 μM | 42 μM | 59 μM |
| T0516-8237 | 1H4 | 9.4 μM | 4.7 μM | 8 μM |
| T5236177 | 1E07 | 2.5 μM | 1.5 μM | 3.2 μM |
| T5251792 | B03 | N/A | N/A | N/A |

Structures of compounds described in the Example are as foll

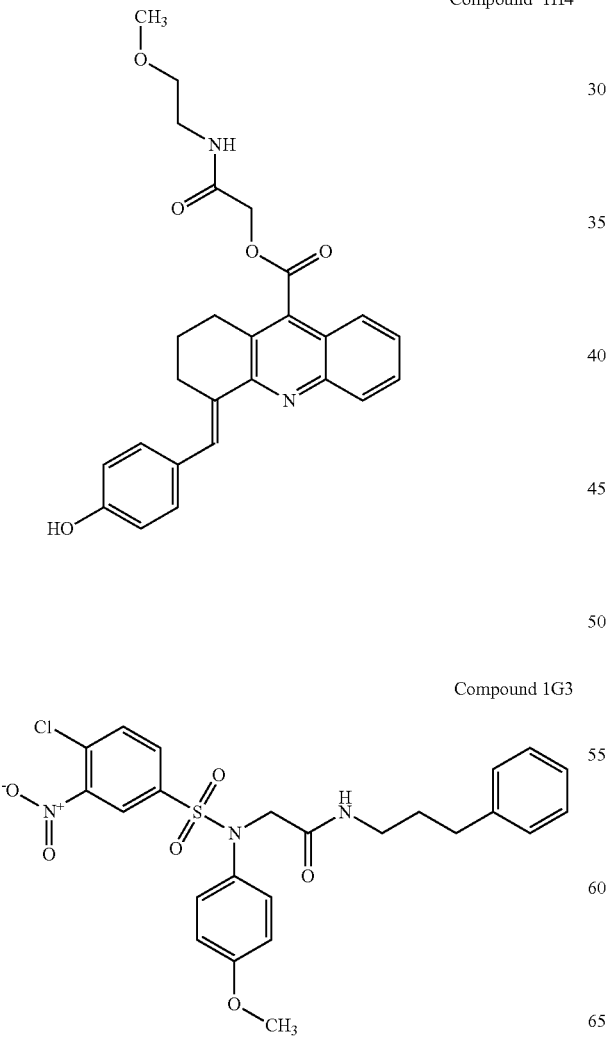

Compound 1H4

Compound 1G3

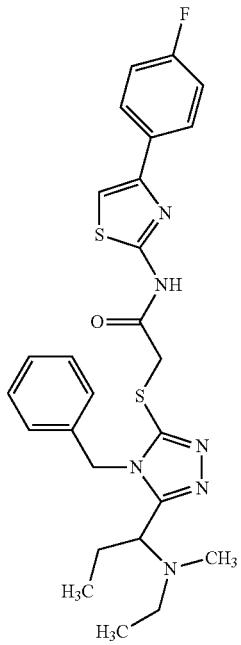

Compound 1C7

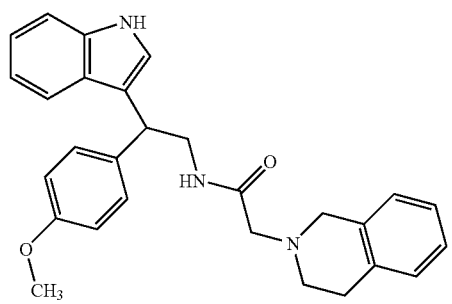

Compound 3C8

What is claimed is:

1. A compound of formula (I) comprising:

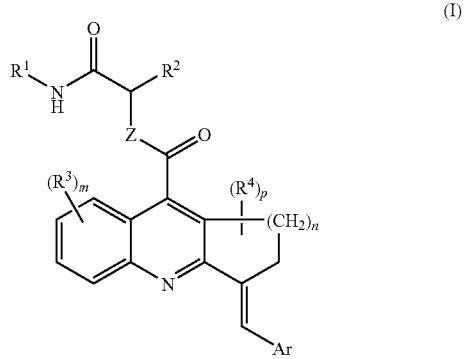

(I)

wherein n is 1 or 2;
Ar is phenyl or thienyl, and is optionally substituted;
each $R^1$ is independently $R^6$, $C(O)R^6$, $C(O)$—$OR^6$, or $C(O)N(R^6)_2$;
$R^2$ is H or optionally substituted C1-C6 alkyl, or a group of formula —$C(O)NH$—$R^1$;
$R^3$ is independently at each occurrence selected from halo, $NO_2$, CN, R, OR, $NR_2$;

S(O)$_q$R, COOR, and CONR$_2$, where each R is independently H, C1-C4 alkyl, or C1-C4 haloalkyl;

m is 0-4;

R$^4$ is R$^6$, halo, =O, COOR$^6$, CO N(R$^6$)$_2$, S(O)$_q$R$^6$, N(R$^6$)$_2$, or OR$^6$;

p is 0-2;

each q is independently 0-2;

Z is O or NR$^5$;

R$^5$ is R$^6$ or C(O)R$^6$; and

R$^6$ is independently at each occurrence selected from H, C1-C6 alkyl, C5-C6 aryl, and (C5-C6-aryl)-C1-C6 alkyl, where each alkyl and aryl is optionally substituted;

provided that n is 2 when Z is O and Ar represents para-halophenyl;

or a pharmaceutically acceptable salt thereof.

2. The compound of claim 1, comprising a pharmaceutically acceptable salt of a compound of formula I.

3. The compound of claim 1, wherein Z is O.

4. The compound of claim 1, wherein n is 1.

5. The compound of claim 1, wherein n is 2.

6. The compound of claim 1, wherein R$^2$ is H or C1-C4 alkyl.

7. The compound of claim 1, wherein Ar is optionally substituted phenyl.

8. The compound of claim 1, wherein Ar is optionally substituted 2-thienyl.

9. The compound of claim 1, wherein Ar is optionally substituted 3-thienyl.

10. A pharmaceutical composition comprising a compound of formula (I) admixed with at least one pharmaceutically acceptable excipient or diluent.

11. A method for treating a subject infected with or at risk of infection with HIV-1, the method comprising administering to a subject in need of such treatment a therapeutically effective amount of a compound of formula (I).

12. A method to inhibit replication of HIV-1 virus, comprising contacting the HIV-1 virus or a cell containing the HIV-1 virus with a compound of formula (I).

13. A compound selected from the group consisting of

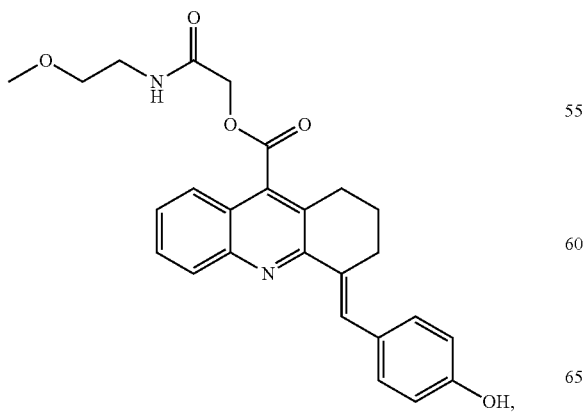

Compound A

-continued

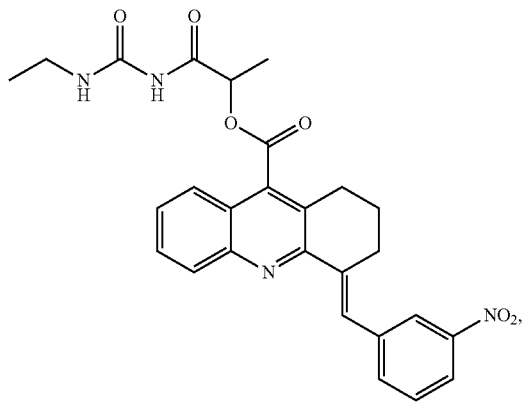

Compound B

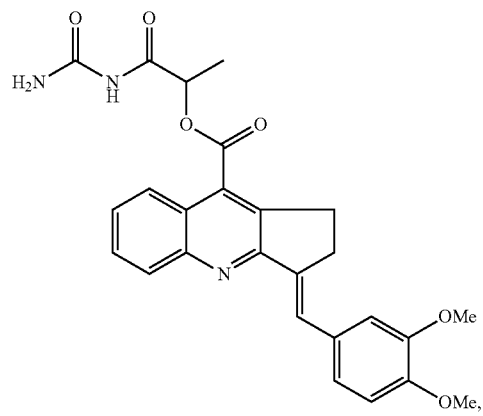

Compound C

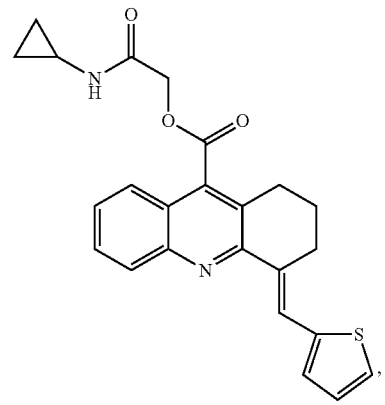

Compound D

Compound E

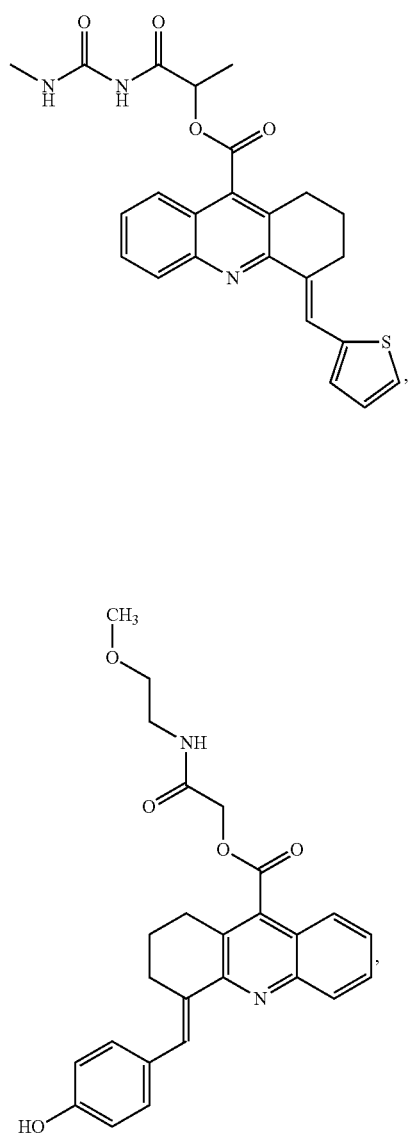

Compound 1H4

Compound 1G3

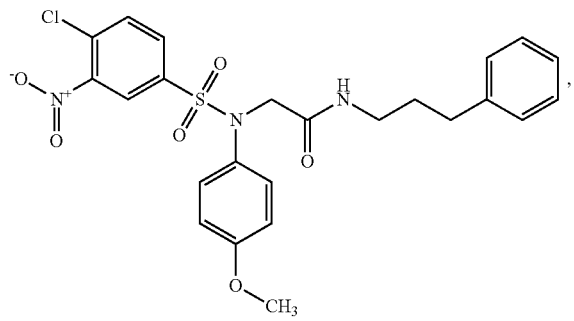

Compound 1C7

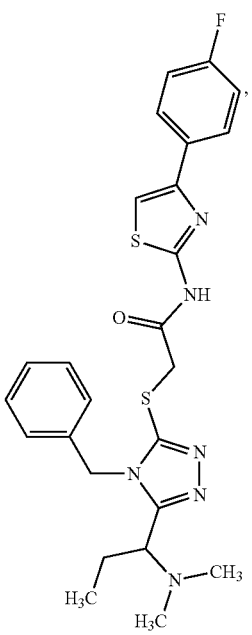

Compound 3C8 and pharmaceutically acceptable salts of these compounds.

14. A method for treating a subject infected with or at risk of infection with HIV-1, the method comprising administering to a subject in need of such treatment a therapeutically effective amount of a compound selected from the group consisting of Compound A

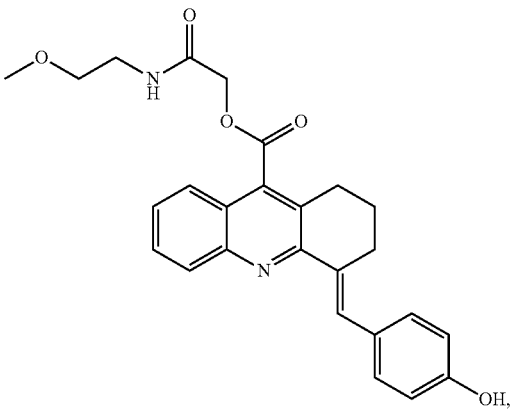

Compound B
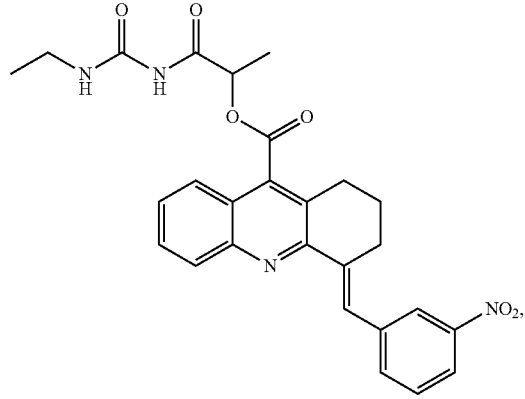
Compound C
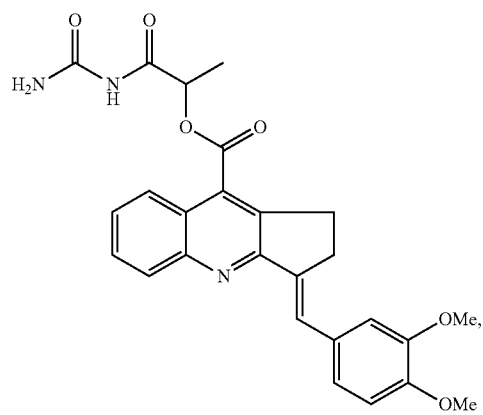
Compound D
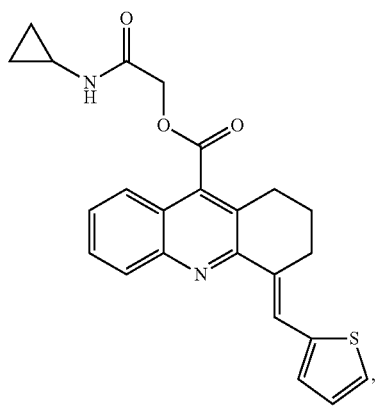
Compound E
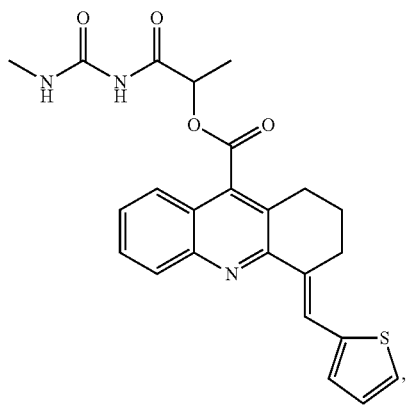
Compound 1H4
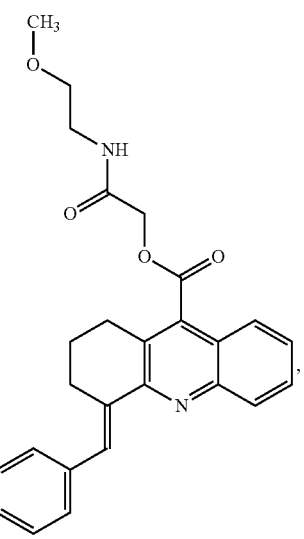
Compound 1G3
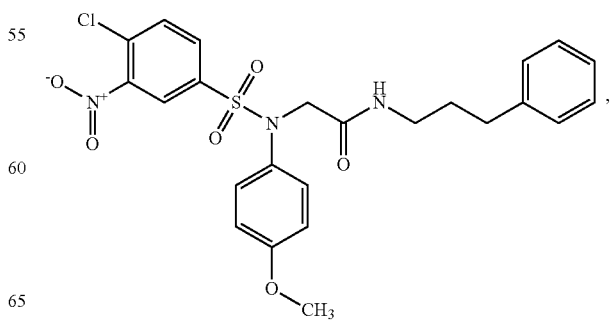

Compound 1C7
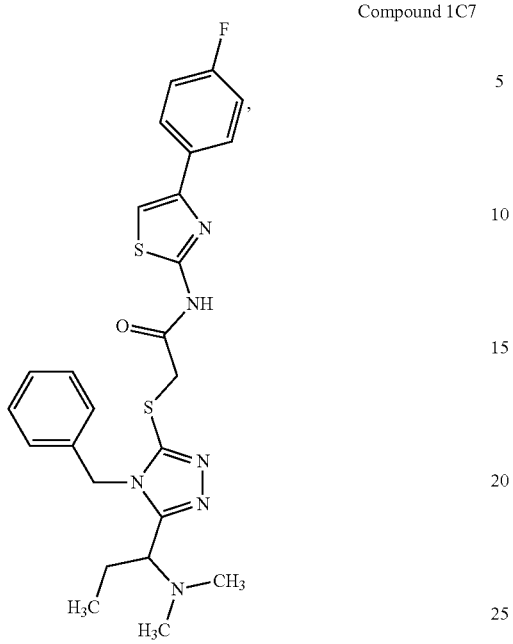
Compound B
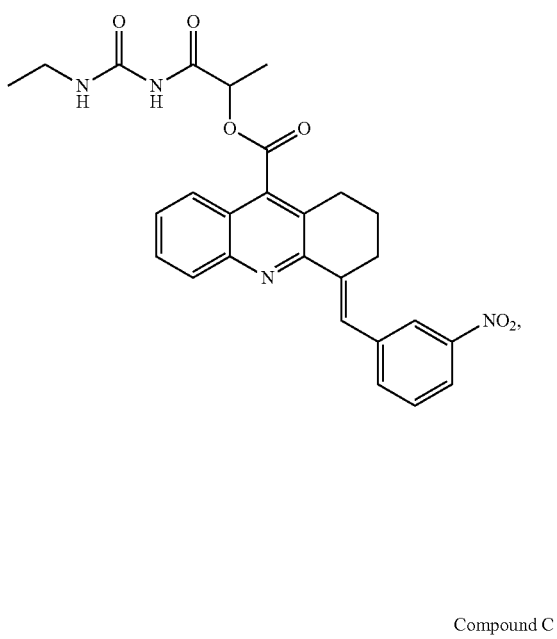
Compound 3C8
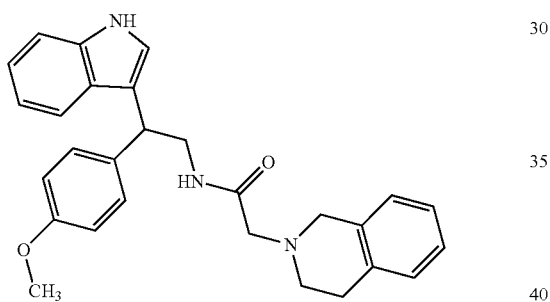
Compound C
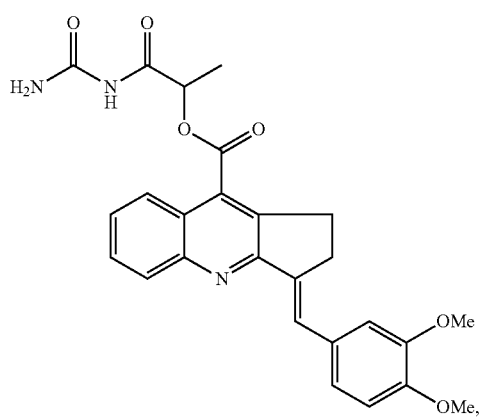
and pharmaceutically acceptable salts of these compounds.
15. A method to inhibit replication of HIV-1 virus, comprising contacting the HIV-1 virus or a cell containing the HIV-1 virus with a compound selected from the group consisting of Compound A
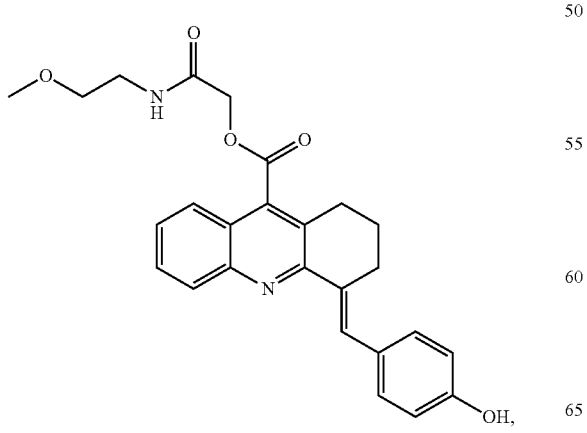
Compound D
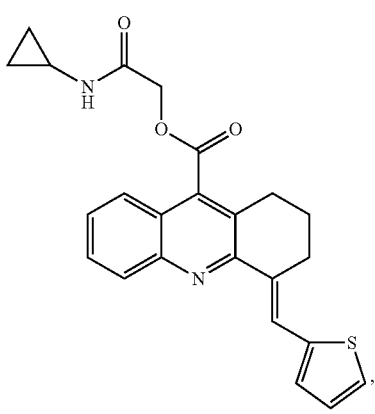

Compound E
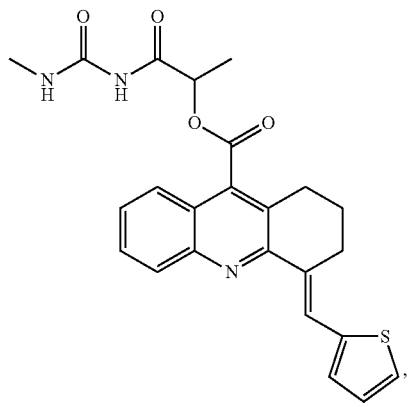
Compound 1H4
Compound 1G3
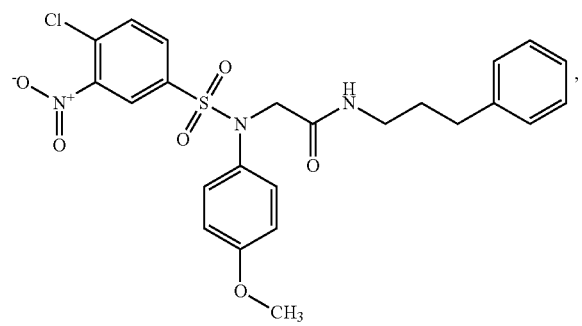
Compound 1C7
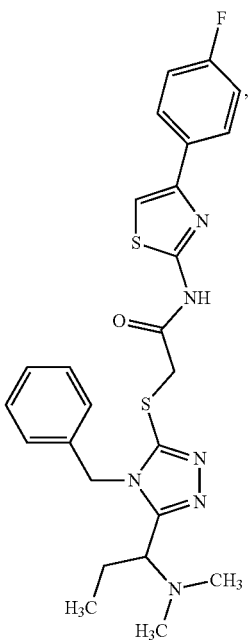
Compound 3C8
and pharmaceutically acceptable salts of these compounds.
* * * * *